US010905856B1

(12) United States Patent
Rayhanabad

(10) Patent No.: US 10,905,856 B1
(45) Date of Patent: Feb. 2, 2021

(54) FISTULA PATCH AND METHOD OF PROVIDING DIALYSIS

(71) Applicant: Simon B. Rayhanabad, Huntington Beach, CA (US)

(72) Inventor: Simon B. Rayhanabad, Huntington Beach, CA (US)

(*) Notice: Subject to any disclaimer, the term of this patent is extended or adjusted under 35 U.S.C. 154(b) by 0 days.

(21) Appl. No.: 16/186,555

(22) Filed: Nov. 11, 2018

Related U.S. Application Data

(60) Provisional application No. 62/585,490, filed on Nov. 13, 2017, provisional application No. 62/599,441, filed on Dec. 15, 2017, provisional application No. 62/634,663, filed on Feb. 23, 2018, provisional application No. 62/673,766, filed on May 18, 2018.

(51) Int. Cl.
| | | |
|---|---|---|
| *A61M 39/00* | (2006.01) | |
| *A61M 25/02* | (2006.01) | |
| *A61M 1/14* | (2006.01) | |
| *A61M 1/36* | (2006.01) | |
| *A61M 39/02* | (2006.01) | |

(52) U.S. Cl.
CPC .............. *A61M 25/02* (2013.01); *A61M 1/14* (2013.01); *A61M 1/3655* (2013.01); *A61M 39/0208* (2013.01); *A61M 39/0247* (2013.01); *A61M 2025/0266* (2013.01); *A61M 2025/0286* (2013.01)

(58) Field of Classification Search
CPC ...................... A61M 39/0208; A61M 39/0247
See application file for complete search history.

(56) References Cited

U.S. PATENT DOCUMENTS

| | | | | |
|---|---|---|---|---|
| 7,828,781 B2* | 11/2010 | Edoga | ................. | A61M 1/3655 604/244 |
| 2011/0213309 A1* | 9/2011 | Young | ................. | A61B 17/0057 604/175 |
| 2012/0245536 A1* | 9/2012 | Gerber | .............. | A61M 39/0208 604/288.02 |

* cited by examiner

*Primary Examiner* — Benjamin J Klein
(74) *Attorney, Agent, or Firm* — Steven R. Vosen

(57) ABSTRACT

An apparatus and method for providing dialysis are described. The apparatus is a patch which provides structural support to a blood vessel, such as vein or fistula. The patch provides a location for puncturing the blood vessel with a needle, either at the puncture site or on the back side to prevent the needle from going through the blood vessel. The patch may also be palpated, allowing health care provider to easily locate a preferred puncture site. The method includes placing the patch on the blood vessel, and using the patch to provide a location for providing dialysis.

17 Claims, 5 Drawing Sheets

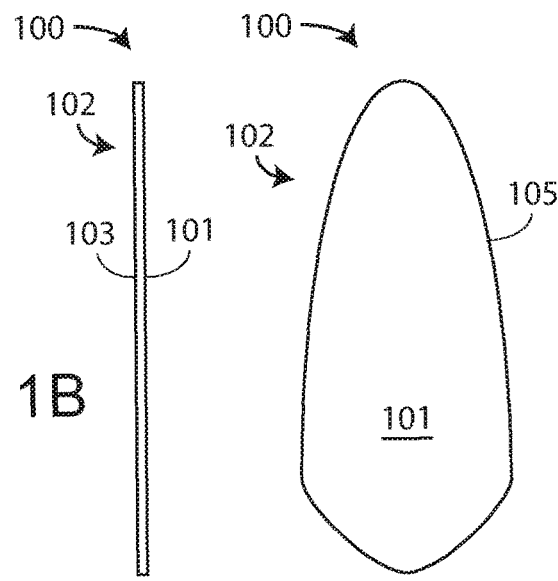
FIG. 1A
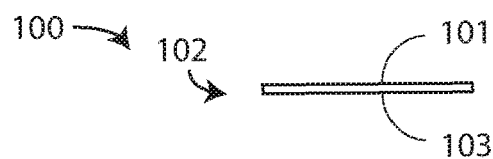
FIG. 1B
FIG. 1C
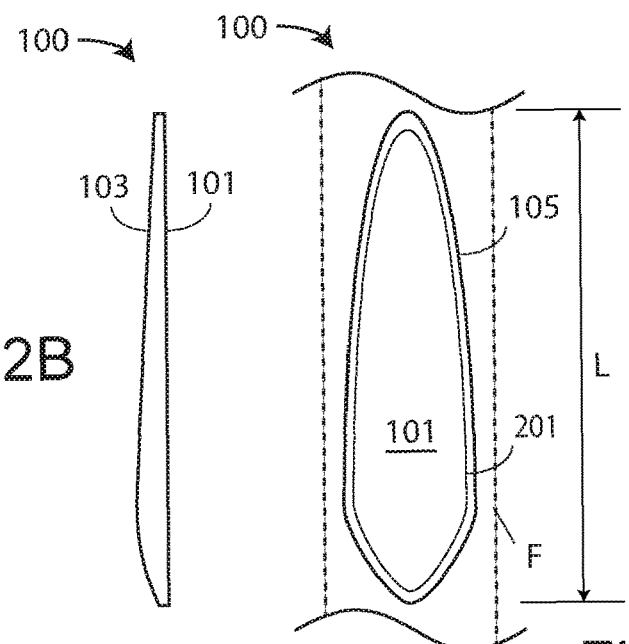
FIG. 2B
FIG. 2A
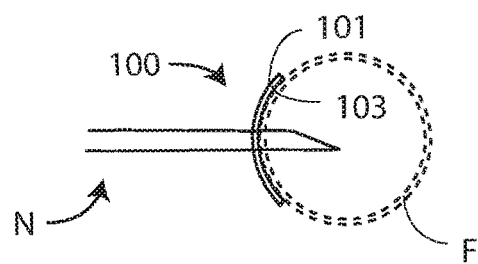
FIG. 2C

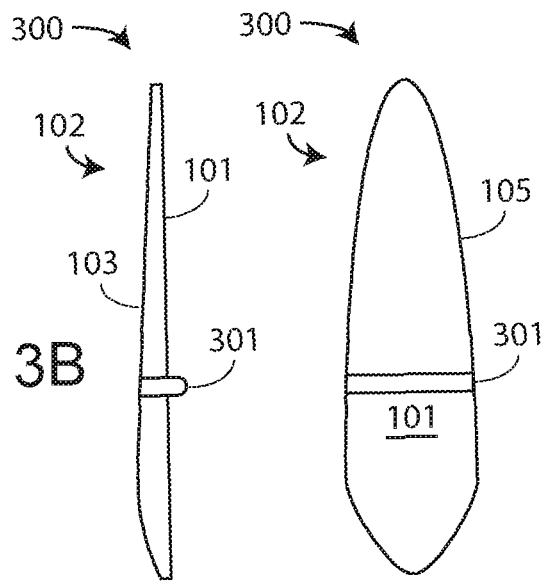
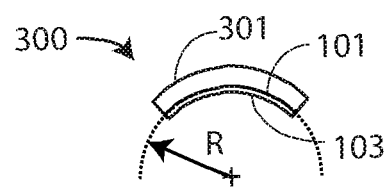
FIG. 3B  FIG. 3A
FIG. 3C
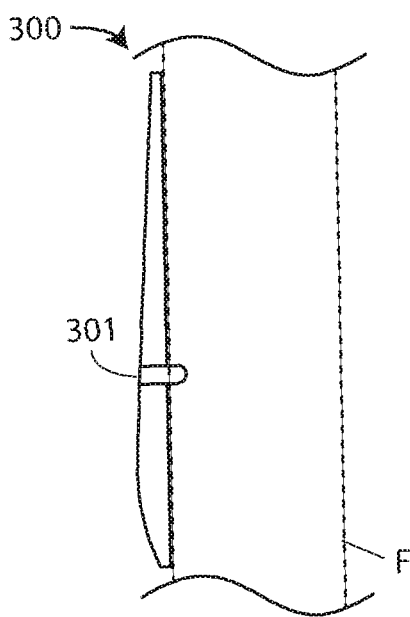
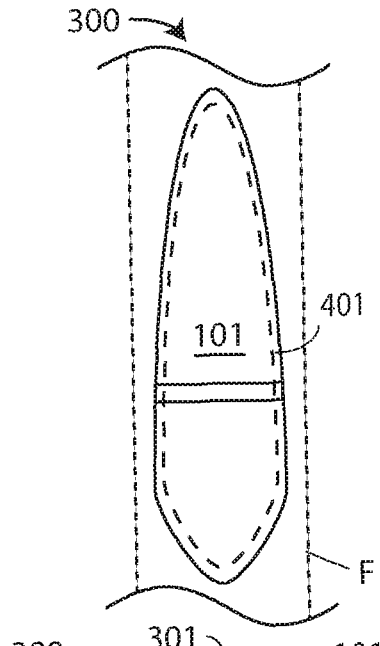
FIG. 4A
FIG. 4B
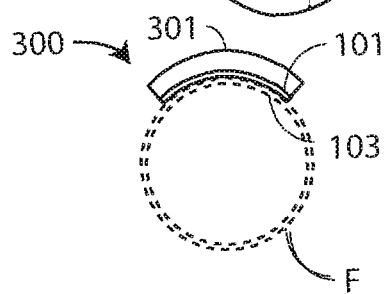
FIG. 4C

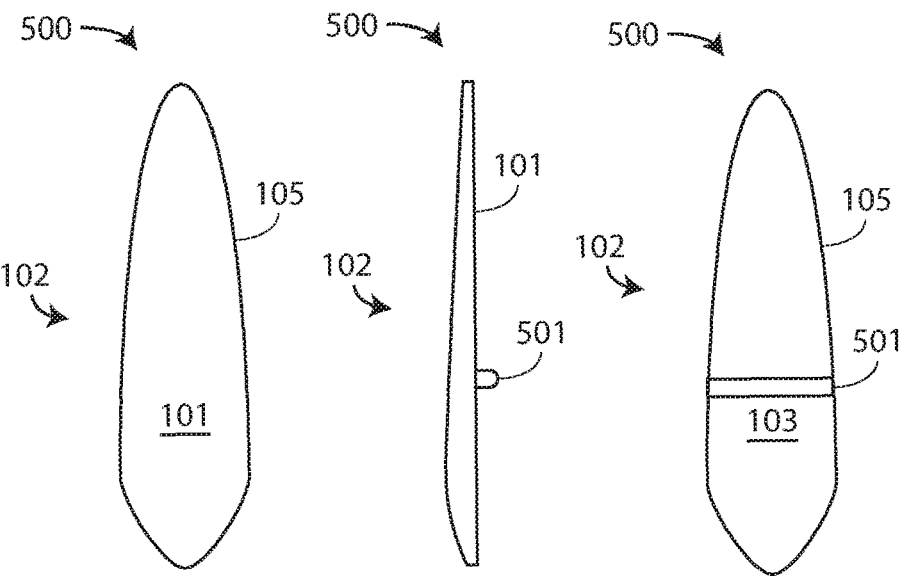
FIG. 5A   FIG. 5B   FIG. 5D
FIG. 5C
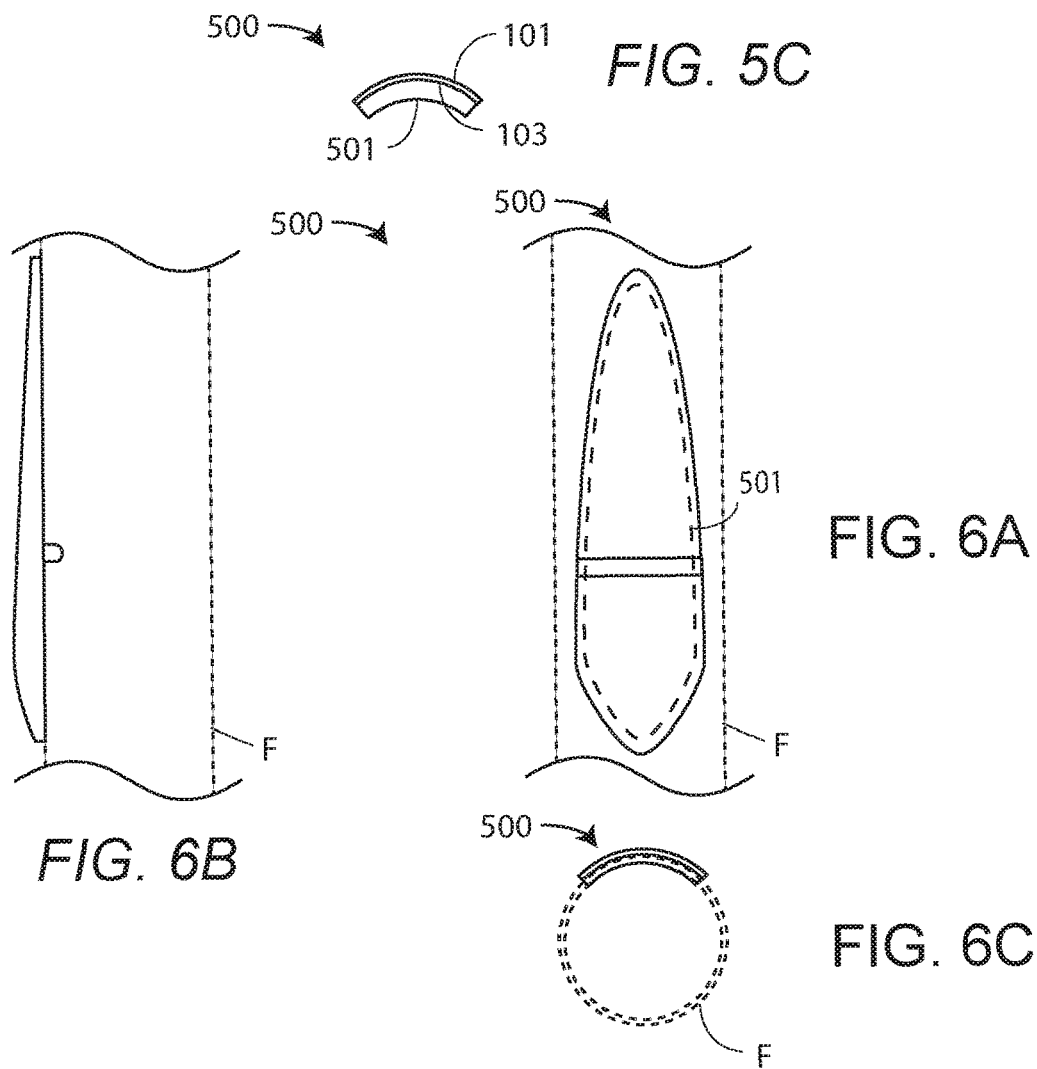
FIG. 6A
FIG. 6B
FIG. 6C

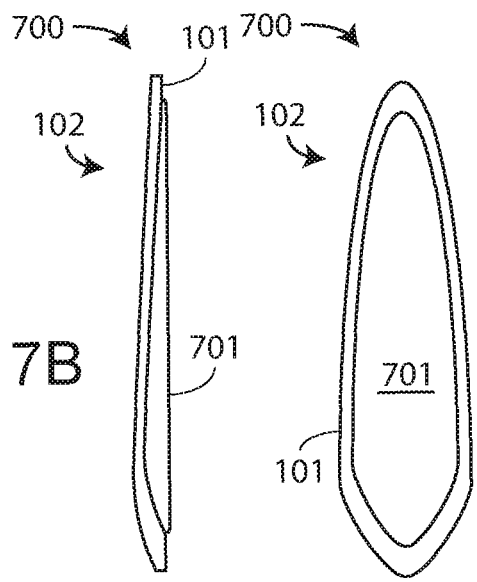
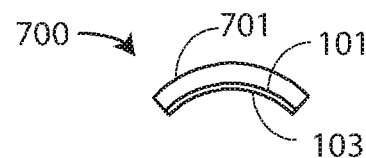
FIG. 7A
FIG. 7B
FIG. 7C
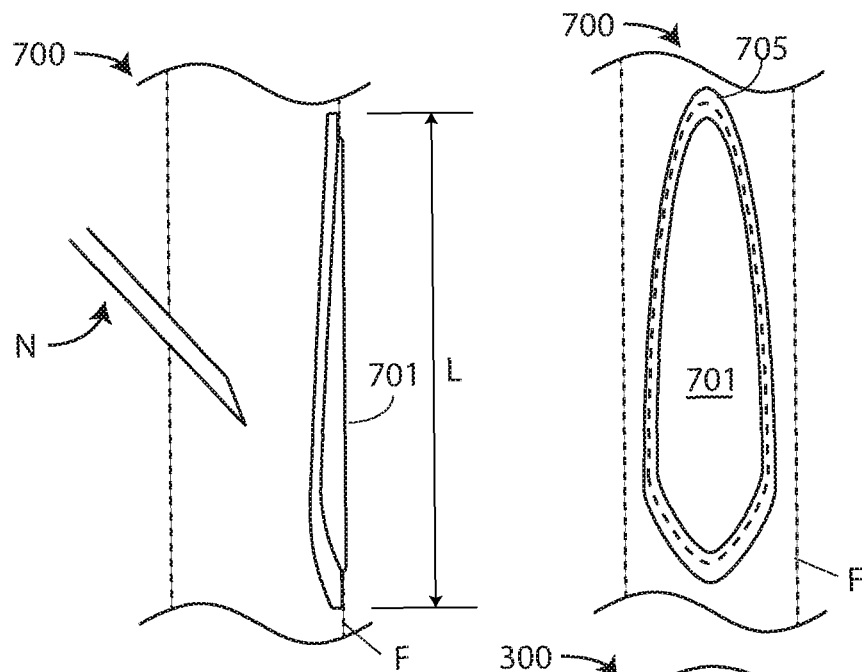
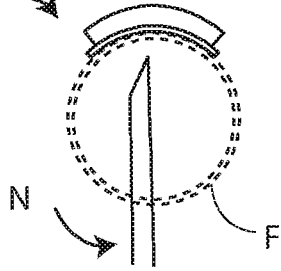
FIG. 8A
FIG. 8B
FIG. 8C

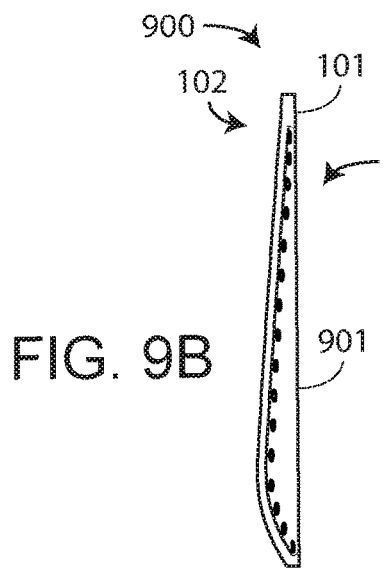
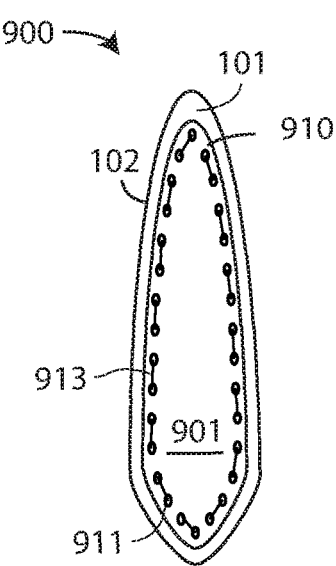
FIG. 9B
FIG. 9A
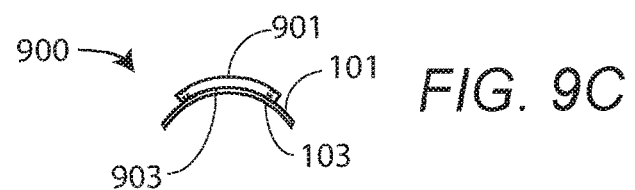
FIG. 9C
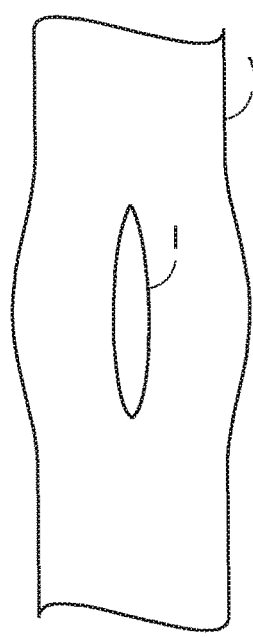
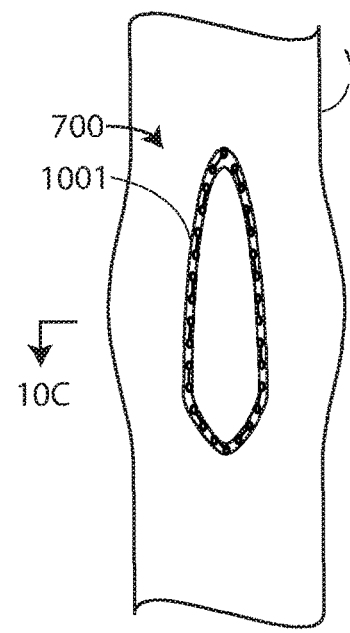
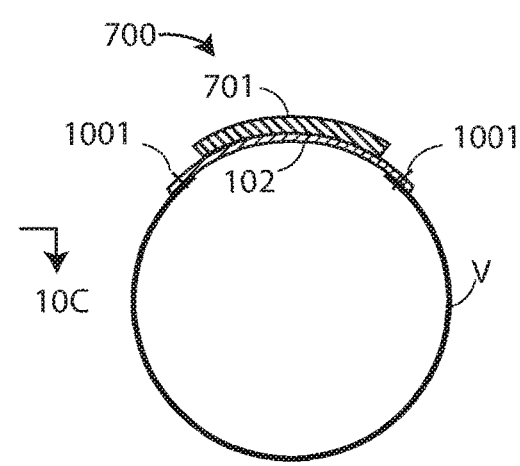
FIG. 10A
FIG. 10B
FIG. 10C

FISTULA PATCH AND METHOD OF PROVIDING DIALYSIS

CROSS-REFERENCE TO RELATED APPLICATIONS

This application claims the benefit of U.S. Provisional Applications No. 62/585,490, filed Nov. 13, 2017, U.S. Provisional Applications No. 62/599,441, filed Dec. 15, 2017, U.S. Provisional Applications No. 62/634,663, filed Feb. 23, 2018, and U.S. Provisional Applications No. 62/673,766, filed May 18, 2018, the contents of which are hereby incorporated by reference in their entirety.

BACKGROUND OF THE INVENTION

Field of the Invention

The present invention generally relates to dialysis, and more particularly to a method and system for surgically preparing a patient for dialysis.

Discussion of the Background

BACKGROUND

In hemodialysis, an artificial kidney is used to remove waste and extra chemicals and fluid from a patient's blood. Typically, blood is removed from a first location in the patient's circulation system, is filtered, and is provided back into the patient at a second location that is downstream from the first location.

Vascular access is obtained from a minor surgical procedure to the arm or leg. In some cases, an access is obtained by joining an artery to a vein to form a bigger blood vessel to form a fistula.

The nature of hemodialysis requires vascular access that is suitable for repeated puncture and allows a high blood flow rate for high-efficiency hemodialysis with minimal complications. Over time, however, complications may arise, due in part to the weakening of the blood vessels due to repeated puncturing.

There is a need in the art for a device, and method of using such a device, that extends the life of vascular access for hemodialysis.

BRIEF SUMMARY OF THE INVENTION

The present invention overcomes the disadvantages of prior art by providing a patch for a blood vessel.

Certain embodiments provide a patch on a blood vessel below the skin to be used for dialysis. The patch includes a rigid portion that can be felt thought the skin, thus facilitating the insertion of the dialysis needle.

Certain other embodiments provide a patch on a blood vessel below the skin to be used for dialysis. Patches proximal the skin may then be used for repeated puncturing of the blood vessel for dialysis.

Certain embodiments provide a patch on a blood vessel below the skin to be used for dialysis. Patches distal, when sufficiently rigid, may prevent needles from accidentally puncturing the distal portion of the blood vessel.

Certain embodiments provide a method including: affixing a patch to a blood vessel of a patient, such that the patch at least partially covers the surface of the blood vessel along a length of the blood vessel; and surgically providing the blood vessel and patch below the surface of the skin of the patient.

In various embodiments, the affixing includes suturing the patch to the blood vessel on either a side of the blood vessel proximal to the skin or a side of the blood vessel distal to the skin.

In various other embodiments, the affixing includes suturing a first patch to the blood vessel on either a side of the blood vessel proximal to the skin or a second side to the blood vessel distal to the skin.

Certain embodiments provide a method including: inserting a needle connected to the catheter of a hemodialysis machine through a patch on a proximal side of a blood vessel of a patient and into the blood vessel.

Certain embodiments provide a patch for a blood vessel. The patch includes: a first portion having defining a width and a length; and a second portion that is more rigid than the first portion and has a shape semicircular shape. When the first portion is affixed to the blood vessel, the semicircular shape reinforces the tubular shape of the blood vessel.

These features together with the various ancillary provisions and features which will become apparent to those skilled in the art from the following detailed description, are attained by the patch of the present invention, preferred embodiments thereof being shown with reference to the accompanying drawings, by way of example only, wherein:

BRIEF DESCRIPTION OF THE SEVERAL VIEWS OF THE DRAWING

FIG. 1A is a top view of a first embodiment patch;
FIG. 1B is a side view of the patch of FIG. 1A;
FIG. 1C is a front view of the patch of FIG. 1A;
FIG. 2A is a top view of the patch of FIG. 1A as attached to a fistula;
FIG. 2B is a side view of the patch of FIG. 1A as attached to a fistula;
FIG. 2C is a front view of patch of FIG. 1A as attached to a fistula;
FIG. 3A is a top view of a second embodiment patch;
FIG. 3B is a side view of the patch of FIG. 3A;
FIG. 3C is a front view of the patch of FIG. 3A;
FIG. 4A is a top view of the patch of FIG. 3A as attached to a fistula;
FIG. 4B is a side view of the patch of FIG. 3A as attached to a fistula;
FIG. 4C is a front view of patch of FIG. 3A as attached to a fistula;
FIG. 5A is a top view of a third embodiment patch;
FIG. 5B is a side view of the patch of FIG. 5A;
FIG. 5C is a front view of the patch of FIG. 5A;
FIG. 5D is a back view of the patch of FIG. 5A;
FIG. 6A is a top view of the patch of FIG. 5A as attached to a fistula;
FIG. 6B is a side view of the patch of FIG. 5A as attached to a fistula;
FIG. 6C is a front view of patch of FIG. 5A as attached to a fistula;
FIG. 7A is a top view of a fourth embodiment patch;
FIG. 7B is a side view of the patch of FIG. 7A;
FIG. 7C is a front view of the patch of FIG. 7A;
FIG. 8A is a top view of the patch of FIG. 7A as attached to a fistula;
FIG. 8B is a side view of the patch of FIG. 7A as attached to a fistula;

FIG. 8C is a front view of patch of FIG. 7A as attached to a fistula.

FIG. 9A is a top view of a fifth embodiment patch;

FIG. 9B is a side view of the patch of FIG. 9A;

FIG. 9C is a back view of the patch of FIG. 9A; and

FIGS. 10A, 10B, and 10C illustrate one use of the patch of FIG. 7A, where FIG. 10A shows an incision to a vein, FIG. 10B shows the patch sewn into the vein, and FIG. 10C is sectional view 10C-10C of FIG. 10B.

Reference symbols are used in the Figures to indicate certain components, aspects or features shown therein, with reference symbols common to more than one Figure indicating like components, aspects or features shown therein.

DETAILED DESCRIPTION OF THE INVENTION

Embodiments are presented for a patch which is an aid to providing hemodialysis to a patient. The Specification and Figures illustrate various patches, which are affixed to fistula and which are then then surgically placed below the skin of a patient. Hemodialysis is thus provided by inserting the hemodialysis needle through the skin and then patch, and into the vein or fistula. The term "blood vessel" is used here to denote any blood-carrying vessel, including both natural and surgically provided vessels, such as a surgically provided fistula.

FIGS. 1A, 1B, and 1C are a top, side, and front view, respectively, of a first embodiment patch 100. Patch 100 includes a thickness of material 102 having an outer edge 105, a side 103 for placing against a patient's fistula, and a side 101 opposing side 103.

In one embodiment, material 102 is a biocompatible material, such as polytetrafluoroethylene (PTFE), formed into a fabric, such as Gore-Tex (W. L. Gore and Associates, Newark, Del.). The thickness of material 102 may be, for example and without limitation, approximately 0.50 mm, or may be 0.25 mm, 0.50 mm, 0.75 mm, or 1.00 mm.

In one embodiment, side 103 includes an optional coating 103 is provided as a barrier between the patient's fistula and material 102. Coating 103 may, for example and without limitation, have bactericidal properties, such as a coating of silver.

In another embodiment, material 102 is soft enough to enable a surgeon to sew the the material, such as outer edge 105, to a blood vessel FIGS. 2A, 2B, and 2C are a top, side, and front view, respectively, of the patch 100 as being attached to a fistula F. The attachment to a fistula is meant to be illustrative and is not meant to limit the scope of the invention. Thus, while patch 100 is shown being attached to a fistula, and being used for providing hemodialysis, it will be understood by those skilled in the art that patch 100, or any of the other patches described herein, are useful in providing structural support to body parts, such as, in general, blood vessels, and may be so used. Thus, for example and without limitation, the inventive patch may be placed on a vein to provide structural support to the vein.

In one embodiment, patch 100 is applied to fistula F by placing one side of patch 100, such as side 103, against fistula F and suturing material 102 near edge 105, as illustrated by dashed line 201.

As is best illustrated in FIG. 2C, patch 100 at least partially extends around the outside of the circumference of the fistula, over a length L of the fistula and on the side of fistula F that is proximal to the skin. FIG. 2C illustrates a needle N, which was previously inserted through the skin of the patient (not shown), and into fistula F somewhere along the fistula length L through patch 100.

The use of patch 100, as in FIG. 2C, allows for repeated puncturing of the blood vessel without damaging the wall of the blood vessel. Patch 100 may also be located by palpation, allowing easier access to the blood vessel.

FIGS. 3A, 3B, and 3C are a top, side, and front view, respectively, of a second embodiment patch 300, which is generally similar to patch 100 in construction and use, except as explicitly noted.

Patch 300 includes a portion that stiffens, or reinforces, the patch, which is illustrated as reinforcement 301. Reinforcement 301 is more rigid than material 102, due to the material used or the the shape or thickness of the reinforcement, and is in general provides a curvature to the patch 300. Thus, for example, reinforcement 301 may have a semicircular shape to match that of fistula F, as shown by radius R in FIG. 3C.

Reinforcement 301 may be formed integral with patch 300, or may be formed from the same or a different material that is affixed to the patch. FIGS. 3A, 3B, and 3C illustrate, for example and without limitation, a reinforcement 301 on side 101 having a length and circular cross-section, and which is bent to have a curvature that closely matches the curvature of the fistula to which it will be attached. In certain embodiment, reinforcement 301 is deformable and may be shaped by hand to change the curvature of patch 300. In one embodiment, reinforcement 301 is formed from a biocompatible material, such as polytetrafluoroethylene (PTFE), formed into a fabric, such as Gore-Tex (W. L. Gore and Associates, Newark, Del.), or a metal such as stainless steel or titanium.

FIGS. 4A, 4B, and 4C are a top, side, and front view, respectively, of the patch 300 as attached to fistula F. In one embodiment, patch 300 is applied to fistula F by placing side 103 against fistula F and suturing material 102 near edge 105, as illustrated by dashed line 401. FIG. 4C illustrates how the curvature of patch 300 matches or approximates the curvature of fistula F. In one embodiment, patch 300 is provided on the side of fistula F that is proximal to the skin, and is used in a matter similar to that shown in FIG. 2C.

FIGS. 5A, 5B, 5C, and 5D are a top, side, front and back view of a third embodiment patch 500, which is generally similar to patch 100 or 300 in construction and use, except as explicitly noted. In one embodiment, reinforcement element 501 is generally similar to reinforcement element 301, but is affixed to side 103.

FIGS. 6A, 6B, and 6C are a top, side, and front view, respectively, of the patch 500 as attached to fistula F. In one embodiment, patch 500 is applied to fistula F by placing one side of patch 500, such as side 103 against fistula F and suturing material 102 near edge 105, as illustrated by dashed line 501.

In one embodiment, a patient is prepared for hemodialysis by forming a fistula from an artery and a vein of the patient, as is known in the art, and then by covering at least a portion of the outer surface of the fistula with a patch, which may be similar to patch 100, 300, or 500. The fistula and patch is then surgically placed below the skin of a patient. In preparing for hemodialysis, the catheter of the hemodialysis machine is place through the skin (not shown), through the patch, and into the fistula.

In one embodiment, patch 500 is provided on the side of fistula F that is proximal to the skin, and is used in a matter similar to that shown in FIG. 2C.

FIGS. 7A, 7B, and 7C are a top, side, front and back view of a fourth embodiment patch 700, which is generally similar to patch 100, 300 or 500 in construction and use, except as explicitly noted.

Patch 700 includes a reinforcement 701 which is attached to side 101. Reinforcement 701 covers substantially all of side 101, except for a border that protrudes from the edge of the reinforcement, and allows for stitching material 102 to the fistula. In one embodiment, reinforcement 701 is formed from a biocompatible material, such as polytetrafluoroethylene (PTFE), formed into a fabric, such as Gore-Tex (W. L. Gore and Associates, Newark, Del.), or a metal, such as a stainless steel or titanium. In yet another alternative embodiment, reinforcement 701 is a layered material, and may have a layer of a metal with a coating of a biocompatible material. In another embodiment, the side of reinforcement 701 facing the interior of the fistula has surface features such as a roughened surface, or a surface covered with holes or protuberances on the order of the size of the tip needle N. The surface features of reinforcement 701 prevents the tip of needle from moving along the reinforcement element, and thus assist in making sure that the needle, when inserted into the patch, does not slip off of the edge of the patch and puncture an unprotected portion of the fistula.

FIGS. 8A, 8B, and 8C are a top, side, and front view, respectively, of the patch 700 as attached to fistula F. As noted above, the purpose of patch 700 is to prevent puncture of the back side of fistula F by needle N.

In one embodiment, patch 700 is applied to fistula F by placing one side of patch 700, such as side 103 against fistula F and suturing material 102 near edge 105, as illustrated by dashed line 705. Patch 700 is placed on the side of the fistula that is distal from the skin, and thus from where a needle N is inserted, as shown in FIGS. 8B and 8C. Specifically, the needle N is inserted through the fistula somewhere along the fistula length L which is covered by patch 700. Reinforcement 701 is thus sufficiently strong, rigid, dense, or thick to prevent a needle tip from puncturing the material when the reinforcement is provided to fistula F.

FIGS. 9A, 9B, and 9C are a top, side, front and back view of a fifth embodiment patch 900, which is generally similar to patch 100, 300, 500, or 700 in construction and use, except as explicitly noted.

Patch 900 includes a material 102 and reinforcement 910. As shown in FIG. 9C, reinforcement 900 has an outer surface 901 and inner surface 903 and a plurality of holes 913 through the thickness of the reinforcement. Inner surface 903 that is affixed to side 101 of material 102 using thread 911, which passes through material 102 and holes 913. In alternative embodiments, material 102 and reinforcement 910 are affixed using an adhesive or other appropriate means of joining.

As shown in FIG. 9A, reinforcement 901 covers substantially all of side 101, except for a border that protrudes from the edge of the reinforcement, and allows for stitching material 102 to the fistula, as shown above regarding patches 100, 300, 500, and 700.

In certain embodiments, patch 900 is applied to side of fistula F that is distal from the skin, and used as shown for patch 700. That is, patch 900 is rigid enough to prevent puncturing by a needle, and is placed on the back side of the fistula from where the catheter is connected to prevent a second puncture of the fistula.

In one embodiment, reinforcement 901 is formed from a biocompatible material, such as polytetrafluoroethylene (PTFE), formed into a fabric, such as Gore-Tex (W. L. Gore and Associates, Newark, Del.), or a metal, such as a stainless steel or titanium. In another embodiment, the side of reinforcement 901 facing the interior of the fistula has surface features such as a roughened surface, or a surface covered with holes or protuberances on the order of the size of the tip needle N. The surface features of reinforcement 901 prevents the tip of needle from moving along the reinforcement element, and thus assist in making sure that the needle, when inserted into the patch, does not slip off of the edge of the patch and puncture an unprotected portion of the fistula.

FIGS. 10A, 10B, and 10C illustrate one use of the patch 700, where FIG. 10A shows an incision to a vein, FIG. 10B shows the patch sewn into the vein, and FIG. 10C is sectional view 10C-10C of FIG. 10B.

More specifically, FIGS. 10A-10C illustrate the use of patch 700 to enlarge and reinforce a vein V. First, the side of vein V distal from the skin is provided with a longitudinal opening, indicated as incision I in FIG. 10A. Next, with the incision held open to increase the diameter of the vein, the edge of the patch is sewn about the incision. Thus, FIGS. 10B and 10C, show stitches 1001 that join the material 102 of patch 700 to the edges of the the incision on the interior surface of the vein, with reinforcement 701 spanning the open portion of the incision, and thus increasing the size of the vein's lumen. In certain embodiments, reinforcement 701 has a semicircular shape that generally matches the tubular shape of the vein. As illustrate in FIGS. 10B and 10C, patch 700 thus enlarges the diameter of the vein at the patch and reinforces the patched vein with reinforcement 701. Alternatively, patch 700 may be sewn to the outer surface of the vein.

In one embodiment, a patient may be provided with a first patch through which a needle may be inserted for hemodialysis, such as patch 100, 300, or 500, which is provided on a proximal side of fistula F, and with a second patch located on the opposite, distal side of the fistula, such a patch 700 or 900. A needle connected to the catheter of a hemodialysis machine is then inserted through the first patch and into the fistula of the patient and is prevented from puncturing the fistula by the second patch.

In another embodiment, hemodialysis may be provided to a patent by forming a fistula from an an artery and a vein of the patient, as is known in the art, and then covering at least a portion of the outer surface of the fistula with a patch, which may be similar to patch 100, 300, 500, 700, or 900. A needle connected to the catheter of a hemodialysis machine is then inserted through the patch and into the fistula of the patient.

In yet another embodiment, a device is provided for preparing a fistula of a patient for hemodialysis. The device includes a patch, which may be similar to patch 100, 300, 500, 700, or 900 comprises a layer of a biocompatible material, where the patch is sized to cover a portion of the outer surface of the fistula.

In certain embodiments, patch 100, 300, 500, 700, or 900 may be felt though the skin of the patient. This allows the person inserting the needle into the patient to determine the location of patch by palpation, and thus makes it it easier to inert the needle at the proper location.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

I claim:

1. A method comprising:
   affixing a patch including a rigid material to a blood vessel of a patient, where said patch includes a surface, and where the patch is affixed with the surface adjacent to and covering only a portion of a circumference of the blood vessel; and
   surgically providing the blood vessel and the affixed patch below the surface of the skin of the patient,
   such that, when the blood vessel and patch are surgically provided below the surface of the skin, the surface of the patch is located only on a side of the blood vessel distal from the surface of the skin.

2. The method of claim 1, where said affixing includes suturing the patch to the blood vessel.

3. The method of claim 1, further comprising
   inserting a needle connected to the catheter of a hemodialysis machine through the skin and into the blood vessel adjacent to the patch, without puncturing the patch.

4. The method of claim 3, where said surface includes features to prevent the slipping of the tip of the needle along the surface.

5. The method of claim 4, where said features include a roughened surface, protuberances on the surface, or a plurality of holes through the patch.

6. The method of claim 5, where the size of said holes or protuberances are on the order of the size of the tip of the needle.

7. The method of claim 1, where said blood vessel is a vein or a fistula.

8. The method of claim 1, where the patch includes a metal.

9. The method of claim 8, where the metal includes stainless steel or titanium.

10. A method comprising:
    inserting a needle connected to the catheter of a hemodialysis machine through the skin of a patient and into a blood vessel of the patient at a location near a patch on the blood vessel,
    where said patch includes a rigid material that covers only a portion of a circumference of the blood vessel distal from the skin at the insertion location of the needle, and where said inserting does not puncture the patch.

11. The method of claim 10, where said blood vessel is a vein or a fistula.

12. The method of claim 10, where said inserting includes palpating the skin to determine the location of the patch.

13. The method of claim 10, where the patch includes a metal.

14. The method of claim 13, where the metal includes stainless steel or titanium.

15. The method of claim 10, where said patch includes a surface adjacent to a portion of a circumference of the blood vessel, and where said patch surface includes features to prevent the slipping of the tip of the needle along the surface.

16. The method of claim 15, where said features include a roughened surface, protuberances on the surface, or a plurality of holes through the patch.

17. The method of claim 16, where the size of said holes or protuberances are on the order of the size of the tip of the needle.

* * * * *